(12) United States Patent
Reed et al.

(10) Patent No.: US 11,117,129 B2
(45) Date of Patent: Sep. 14, 2021

(54) SYSTEM AND METHOD FOR PREPARATION OF NUCLEOTIDE SOLUTIONS

(71) Applicant: LIFE TECHNOLOGIES CORPORATION, Carlsbad, CA (US)

(72) Inventors: Mark Reed, Menlo Park, CA (US); Zheng (Derek) Xing, Westport, CT (US); David Marran, Durham, CT (US); Earl Zergiebel, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 5 days.

(21) Appl. No.: 16/543,421

(22) Filed: Aug. 16, 2019

(65) Prior Publication Data

US 2020/0055046 A1 Feb. 20, 2020

Related U.S. Application Data

(60) Provisional application No. 62/719,567, filed on Aug. 17, 2018.

(51) Int. Cl.
*B01L 3/00* (2006.01)
*C12Q 1/6874* (2018.01)

(52) U.S. Cl.
CPC ... *B01L 3/502715* (2013.01); *B01L 3/502707* (2013.01); *C12Q 1/6874* (2013.01); *B01L 2200/026* (2013.01); *B01L 2200/06* (2013.01); *B01L 2300/0609* (2013.01); *B01L 2300/0636* (2013.01); *B01L 2300/0848* (2013.01)

(58) Field of Classification Search
CPC ......... B01L 3/502715; B01L 3/502707; B01L 2200/026; B01L 2300/0848; B01L 2200/06; B01L 2300/0609; G01N 35/1095; G01N 2035/0491; C12Q 1/6874
See application file for complete search history.

(56) References Cited

U.S. PATENT DOCUMENTS

| | | |
|---|---|---|
| 2012/0143531 A1 | 6/2012 | Davey et al. |
| 2014/0260118 A1 | 9/2014 | Knight |
| 2015/0289856 A1 | 10/2015 | Saqi et al. |
| 2015/0361488 A1* | 12/2015 | Schultz ............... C12Q 1/6869 506/6 |
| 2018/0105810 A1 | 4/2018 | Dejohn et al. |
| 2018/0230529 A1 | 8/2018 | Schultz et al. |

OTHER PUBLICATIONS

PCT/US2019/046945, Search Report and Written Opinion, dated Jan. 15, 2020.

* cited by examiner

*Primary Examiner* — Joseph G. Dauner

(57) ABSTRACT

In an example, a method for preparing a nucleotide solution includes flowing an aqueous solution from an initial solution storage of a sequencing instrument continuously through a container fluidically coupled to the sequencing instrument, the container comprising a nucleotide concentrate; and collecting the aqueous solution with nucleotide in a storage container.

10 Claims, 12 Drawing Sheets

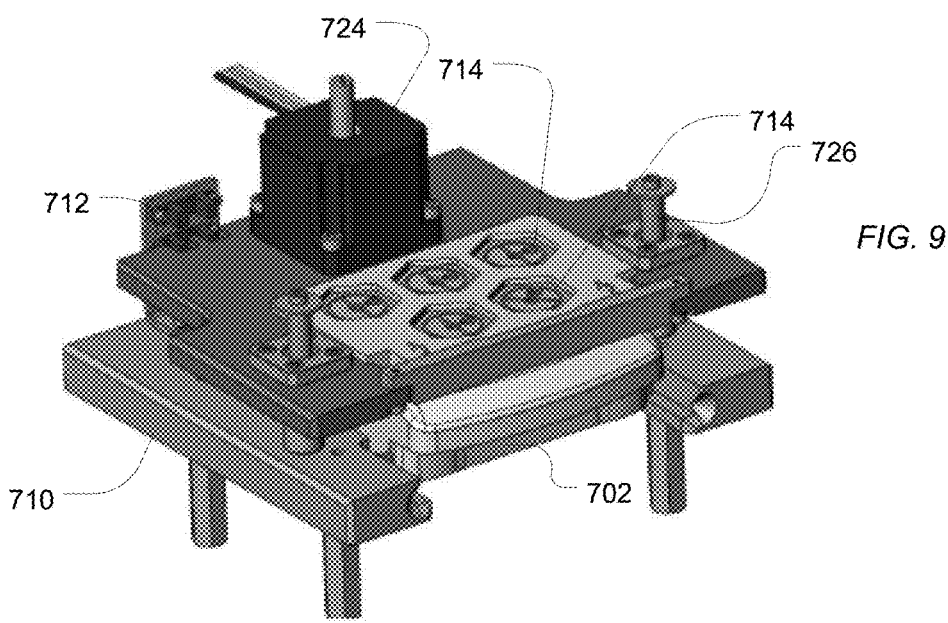
FIG. 9
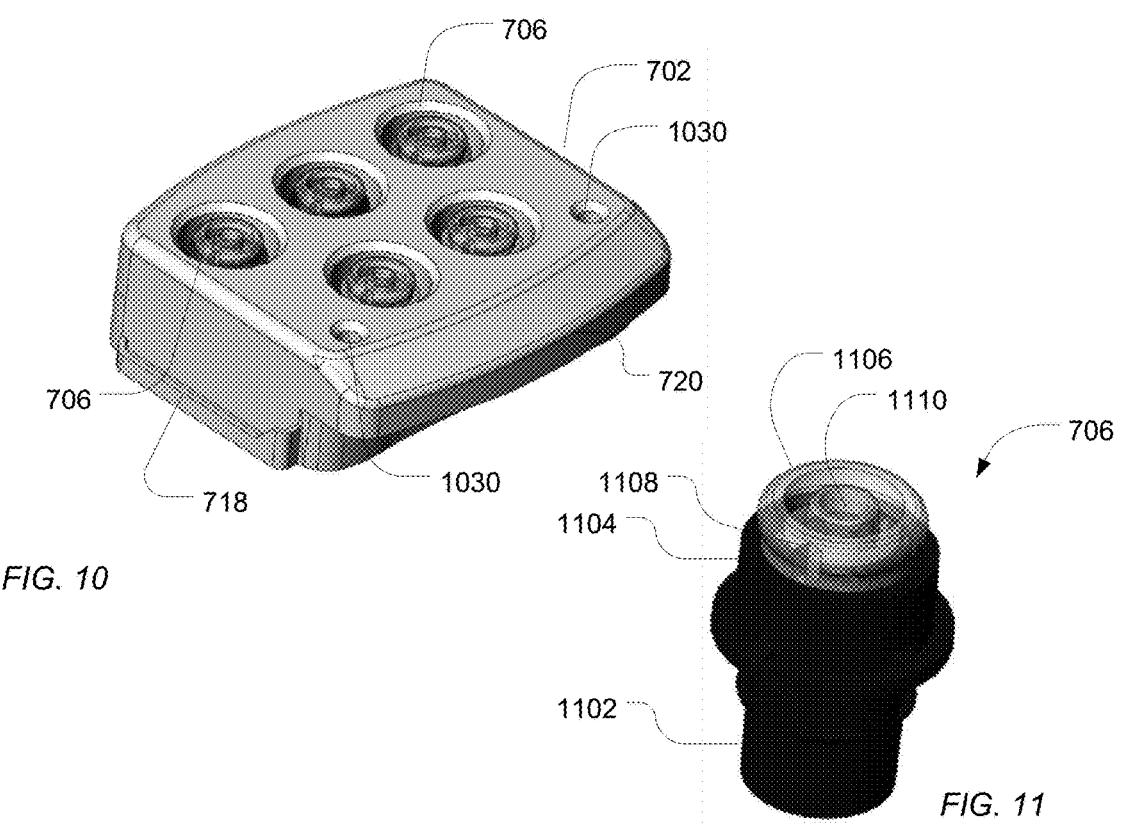
FIG. 10
FIG. 11

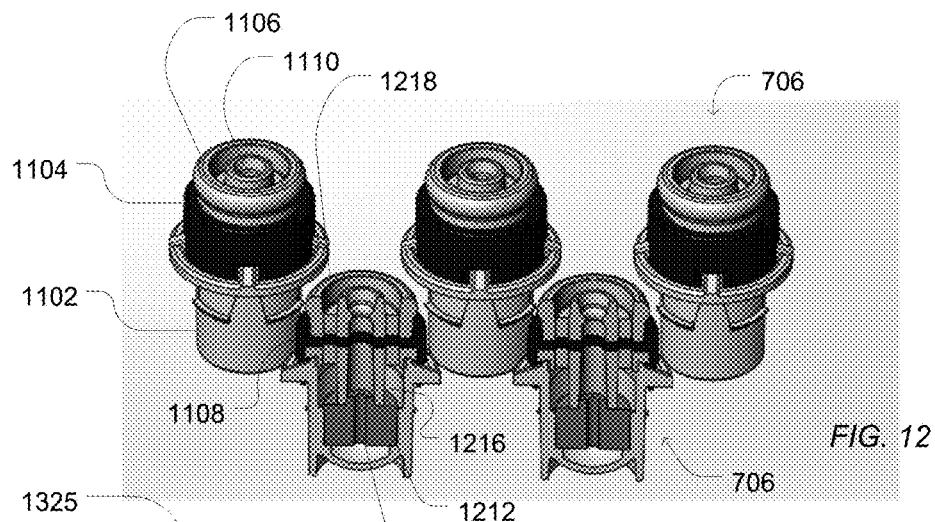
FIG. 12
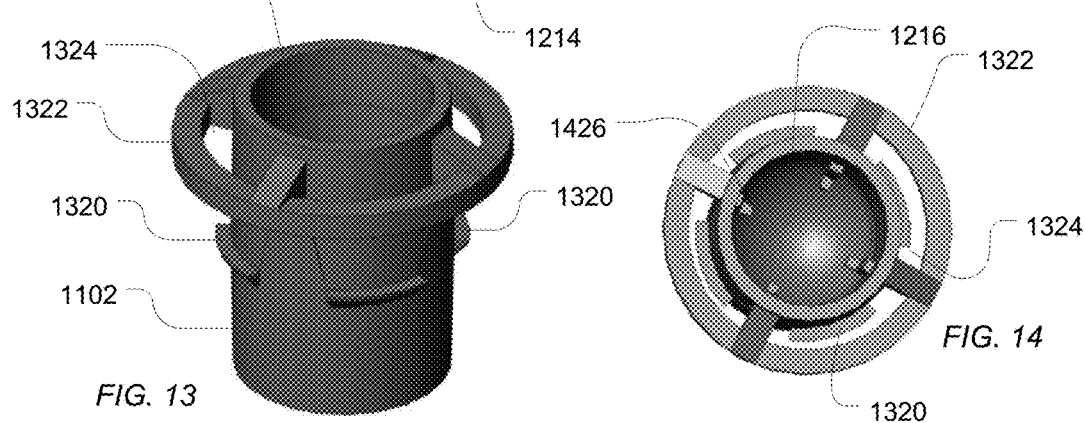
FIG. 13
FIG. 14
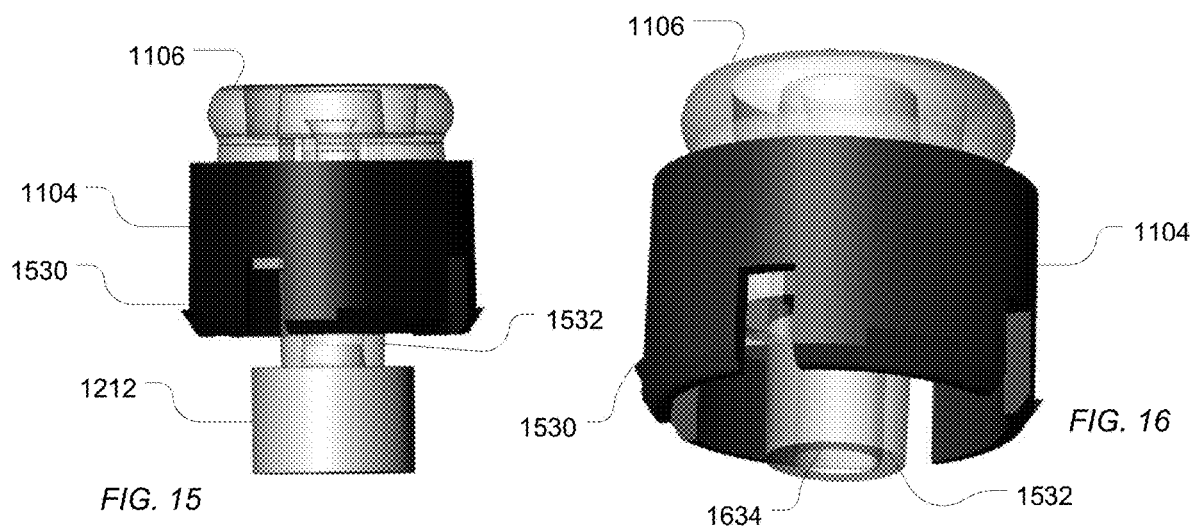
FIG. 15
FIG. 16

SYSTEM AND METHOD FOR PREPARATION OF NUCLEOTIDE SOLUTIONS

CROSS-REFERENCE TO RELATED APPLICATION(S)

This application claims benefit of U.S. Provisional Application No. 62/719,567, filed Aug. 17, 2018, which is incorporated herein by reference in its entirety.

FIELD OF THE DISCLOSURE

This disclosure, in general, relates to systems and method for preparing reagent solutions.

BACKGROUND

Increasingly, biological and medical research is turning to sequencing for enhancing biological studies and medicine. For example, biologist and zoologist are turning to sequencing to study the migration of animals, the evolution of species, and the origins of traits. The medical community is turned sequencing for studying the origins of disease, sensitivity to medicines, and the origins of infection. But, sequencing has historically been an expensive process, thus limiting its practice.

BRIEF DESCRIPTION OF THE DRAWINGS

The present disclosure may be better understood, and its numerous features and advantages made apparent to those skilled in the art by referencing the accompanying drawings.

FIG. 7, FIG. 8, and FIG. 9 include illustrations of example cartridge system.

FIG. 10 includes an illustration of an example cartridge.

FIG. 11, FIG. 12, FIG., 13, FIG. 14, FIG. 15, FIG. 16, FIG. 17, and FIG. 18 include illustrations of an example container and its components for use with a cartridge.

The use of the same reference symbols in different drawings indicates similar or identical items.

DETAILED DESCRIPTION

In an embodiment, a system for preparing reagent solutions includes a cartridge and docking station. The cartridge includes containers having reagent concentrate. The docking station can receive the cartridge and fluidically connect to each of the cartridges. An initial solution can be flowed through each of the containers and into separate reagent storage containers. The system finds particular advantages when used to prepare nucleotide solutions for a sequencing device.

Figure 1:
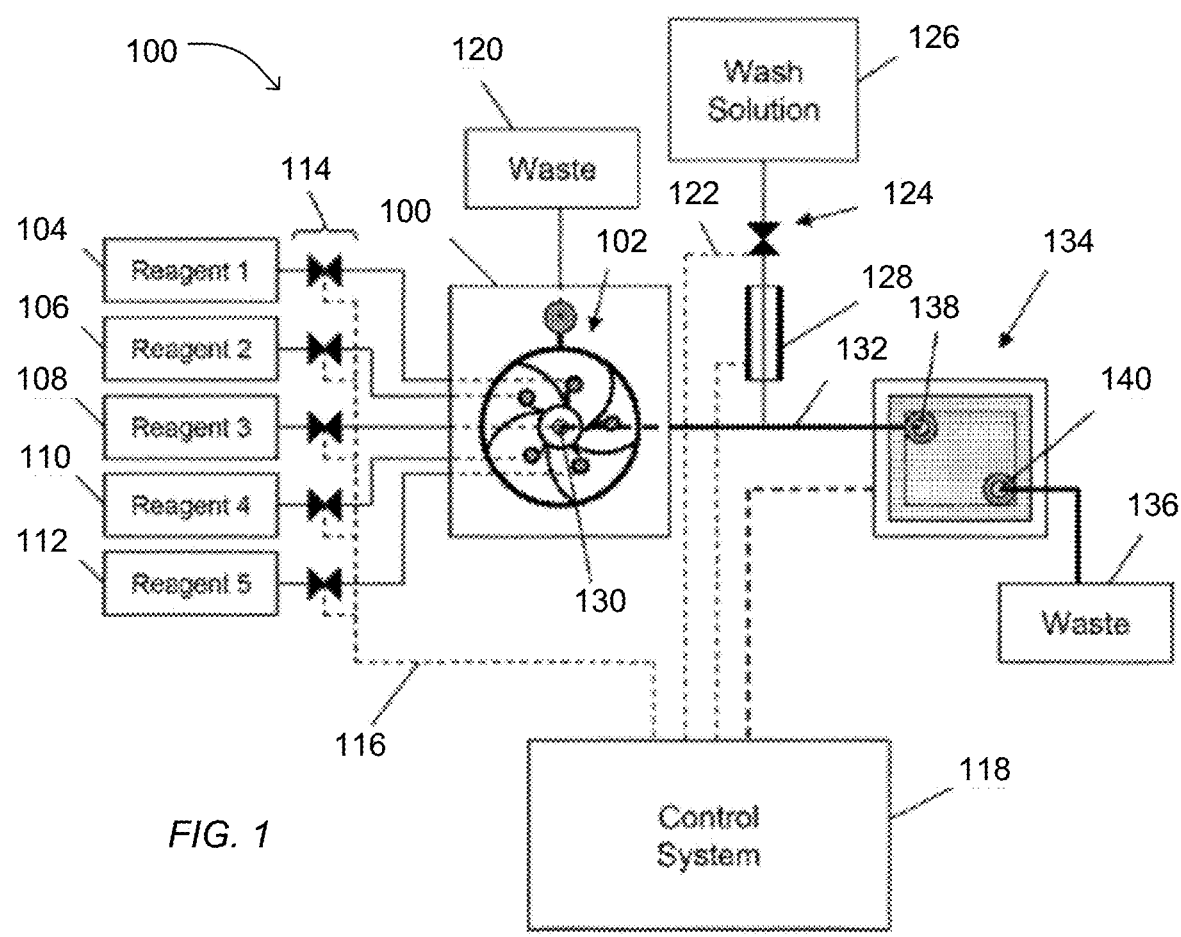
FIG. 1 includes an illustration of an example sequencing system.

FIG. 1 diagrammatically illustrates a system employing a valve, for example, for carrying out pH-based nucleic acid sequencing. Each electronic sensor of the apparatus generates an output signal that depends on the value of a reference voltage. The fluid circuit permits multiple reagents to be delivered to the reaction chambers.

In FIG. 1, system 100 containing fluidics circuit 102 is connected by inlets to at least two reagent reservoirs (104, 106, 108, 110, or 112), to waste reservoir 120, and to biosensor 134 by fluid pathway 132 that connects fluidics node 130 to inlet 138 of biosensor 134 for fluidic communication. Reagents from reservoirs (104, 106, 108, 110, or 112) can be driven to fluidic circuit 102 by a variety of methods including pressure, pumps, such as syringe pumps, gravity feed, and the like, and are selected by control of valves 114. Reagents from the fluidics circuit 102 can be driven through the valves 114 receiving signals from control system 118 to waste container 120. Reagents from the fluidics circuit 102 can also be driven through the biosensor 134 to the waste container 136. The control system 118 includes controllers for valves, which generate signals for opening and closing via electrical connection 116.

The control system 118 also includes controllers for other components of the system, such as wash solution valve 124 connected thereto by electrical connection 122, and reference electrode 128. Control system 118 can also include control and data acquisition functions for biosensor 134. In one mode of operation, fluidic circuit 102 delivers a sequence of selected reagents 1, 2, 3, 4, or 5 to biosensor 134 under programmed control of control system 118, such that in between selected reagent flows, fluidics circuit 102 is primed and washed, and biosensor 134 is washed. Fluids entering biosensor 134 exit through outlet 140 and are deposited in waste container 136 via control of pinch valve regulator 144. The valve 144 is in fluidic communication with the sensor fluid output 140 of the biosensor 134.

Figure 2:
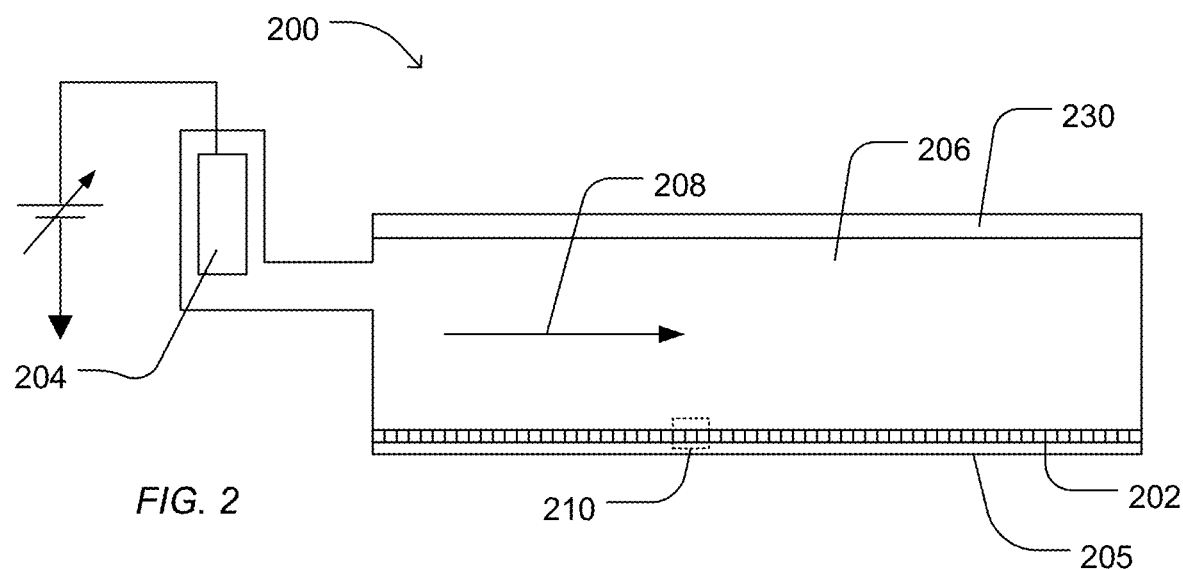
FIG. 2 includes an illustration of an example sequencing device.

The device including the dielectric layer defining the microwell formed from the first access and second access and exposing a sensor pad finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 2 illustrates an expanded and cross-sectional view of a flow cell 200 and illustrates a portion of a flow chamber 206. A reagent flow 208 flows across a surface of a microwell array 202, in which the reagent flow 208 flows over the open ends of microwells of the microwell array 202. The microwell array 202 and a sensor array 205 together may form an integrated unit forming a lower wall (or floor) of flow cell 200. A reference electrode 204 may be fluidly coupled to flow chamber 206. Further, a flow cell cover 230 encapsulates flow chamber 206 to contain reagent flow 208 within a confined region.

Figure 3:
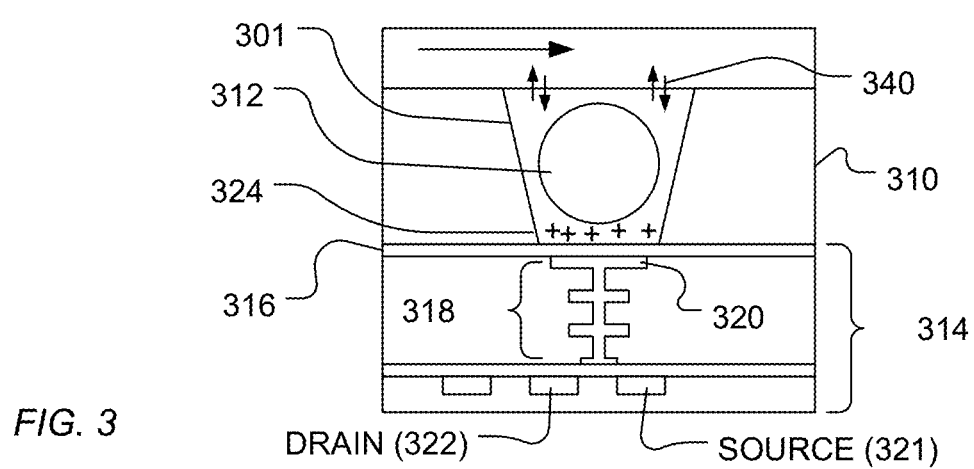
FIG. 3 includes an illustration of an example sequencing component.

FIG. 3 illustrates an expanded view of a microwell 301 and a sensor 314, as illustrated at 210 of FIG. 2. The volume, shape, aspect ratio (such as base width-to-well depth ratio), and other dimensional characteristics of the microwells may be selected based on the nature of the reaction taking place, as well as the reagents, byproducts, or labeling techniques (if any) that are employed. The sensor 314 can be a chemical field-effect transistor (chemFET), more specifically an ion-sensitive FET (ISFET), with a floating gate 318 having a sensor plate 320 optionally separated from the microwell interior by a passivation layer 316. The sensor 314 can be responsive to (and generate an output signal related to) the amount of a charge 324 present on passivation layer 316 opposite the sensor plate 320. Changes in the charge 324 can cause changes in a current between a source 321 and a drain 322 of the chemFET. In turn, the chemFET can be used directly to provide a current-based output signal or indirectly with additional circuitry to provide a voltage-based output signal. Reactants, wash solutions, and other reagents may move in and out of the microwells by a diffusion mechanism 340.

In an embodiment, reactions carried out in the microwell 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, then multiple copies of the same analyte may be analyzed in the microwell 301 at the same time in order to increase the output signal generated. In an embodiment, multiple copies of an analyte may be attached to a solid phase support 312, either before or after deposition into the microwell 301. The solid phase support 312 may be microparticles, nanoparticles, beads, solid or porous comprising gels, or the like. For simplicity and ease of explanation, solid phase support 312 is also referred herein as a particle. For a nucleic acid analyte, multiple, connected copies may be made by rolling circle amplification (RCA), exponential RCA, or like techniques, to produce an amplicon without the need of a solid support.

In particular, the solid phase support can include copies of polynucleotides. In a particular example illustrated in FIG. 4, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

In general, the polymeric particle can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

Figure 4:
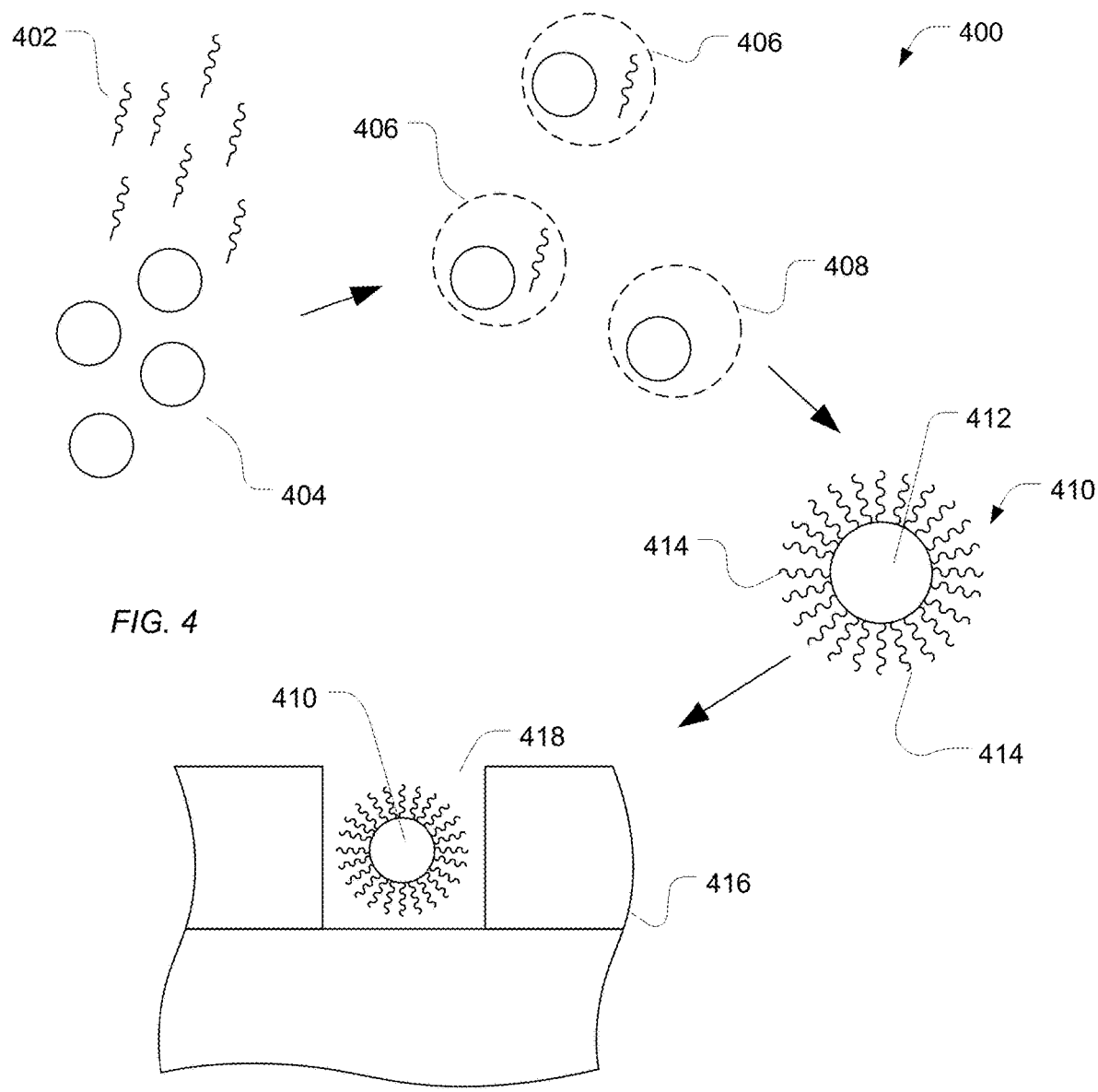
FIG. 4 and FIG. 5 include illustrations of example methods for preparing a sequencing device.

As illustrated in FIG. 4, a plurality of polymeric particles 404 can be placed in a solution along with a plurality of polynucleotides 402. The plurality of particles 404 can be activated or otherwise prepared to bind with the polynucleotides 402. For example, the particles 404 can include an oligonucleotide complementary to a portion of a polynucleotide of the plurality of polynucleotides 402. In another example, the polymeric particles 404 can be modified with target polynucleotides 404 using techniques such as biotin-streptavidin binding. In a particular embodiment, the hydrophilic particles and polynucleotides are subjected to polymerase chain reaction (PCR) amplification or recombinase polymerase amplification (RPA).

For example, dispersed phase droplets 406 or 408 are formed as part of an emulsion and can include a hydrophilic particle or a polynucleotide. In an example, the polynucleotides 402 and the hydrophilic particles 404 are provided in low concentrations and ratios relative to each other such that a single polynucleotide 402 is likely to reside within the same dispersed phase droplets as a single hydrophilic particle 404. Other droplets, such as a droplet 408, can include a single hydrophilic particle and no polynucleotide. Each droplet 406 or 408 can include enzymes, nucleotides, salts or other components sufficient to facilitate duplication of the polynucleotide.

In a particular embodiment, an enzyme such as a polymerase is present, bound to, or is in close proximity to the hydrophilic particle or hydrogel particle of the dispersed phase droplet. In an example, a polymerase is present in the dispersed phase droplet to facilitate duplication of the polynucleotide. A variety of nucleic acid polymerase may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

Following PCR or RPA, particles are formed, such as particle 410, which can include the hydrophilic particle 412 and a plurality of copies 414 of the polynucleotide. While the polynucleotides 414 are illustrated as being on a surface of the particle 410, the polynucleotides can extend within the particle 410. Hydrogel and hydrophilic particles having a low concentration of polymer relative to water can include polynucleotide segments on the interior of and throughout the particle 410 or polynucleotides can reside in pores and other openings. In particular, the particle 410 can permit diffusion of enzymes, nucleotides, primers and reaction products used to monitor the reaction. A high number of polynucleotides per particle produces a better signal.

In embodiments, polymeric particles from an emulsion-breaking procedure can be collected and washed in preparation for sequencing. Collection can be conducted by contacting biotin moieties (e.g., linked to amplified polynucleotide templates which are attached to the polymeric particles) with avidin moieties, and separation away from polymeric particles lacking biotinylated templates. Collected polymeric particles that carry double-stranded template polynucleotides can be denatured to yield single-stranded template polynucleotides for sequencing. Denaturation steps can include treatment with base (e.g., NaOH), formamide, or pyrrolidone.

In an exemplary embodiment, the particle 410 can be utilized in a sequencing device. For example, a sequencing device 416 can include an array of wells 418. The sequencing device 416 can be treated with a wash solution including sulfonic acid, as described above. A particle 410 can be placed within a well 418.

In an example, a primer can be added to the wells 418 or the particle 410 can be pre-exposed to the primer prior to placement in the well 418. In particular, the particle 410 can include bound primer. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 418 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 416 and can migrate to the well 418. Excitation energy can be also provided to the well 418. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 418 can change. Such a change in pH can be detected by ion sensitive field effect transistors (ISFET). As such, a change in pH can be used to generate a signal indicating the order of nucleotides complementary to the polynucleotide of the particle 410.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 4, in another example, a well 418 of the array of wells can be operatively connected to measuring devices. For example, for fluorescent emission methods, a well 418 can be operatively coupled to a light detection device. In the case of ionic detection, the lower surface of the well 418 may be disposed over a sensor pad of an ionic sensor, such as a field effect transistor.

In another embodiment, the solid phase support, such a bead support, can include copies of polynucleotides. In a particular example illustrated in FIG. 5, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

Figure 5:
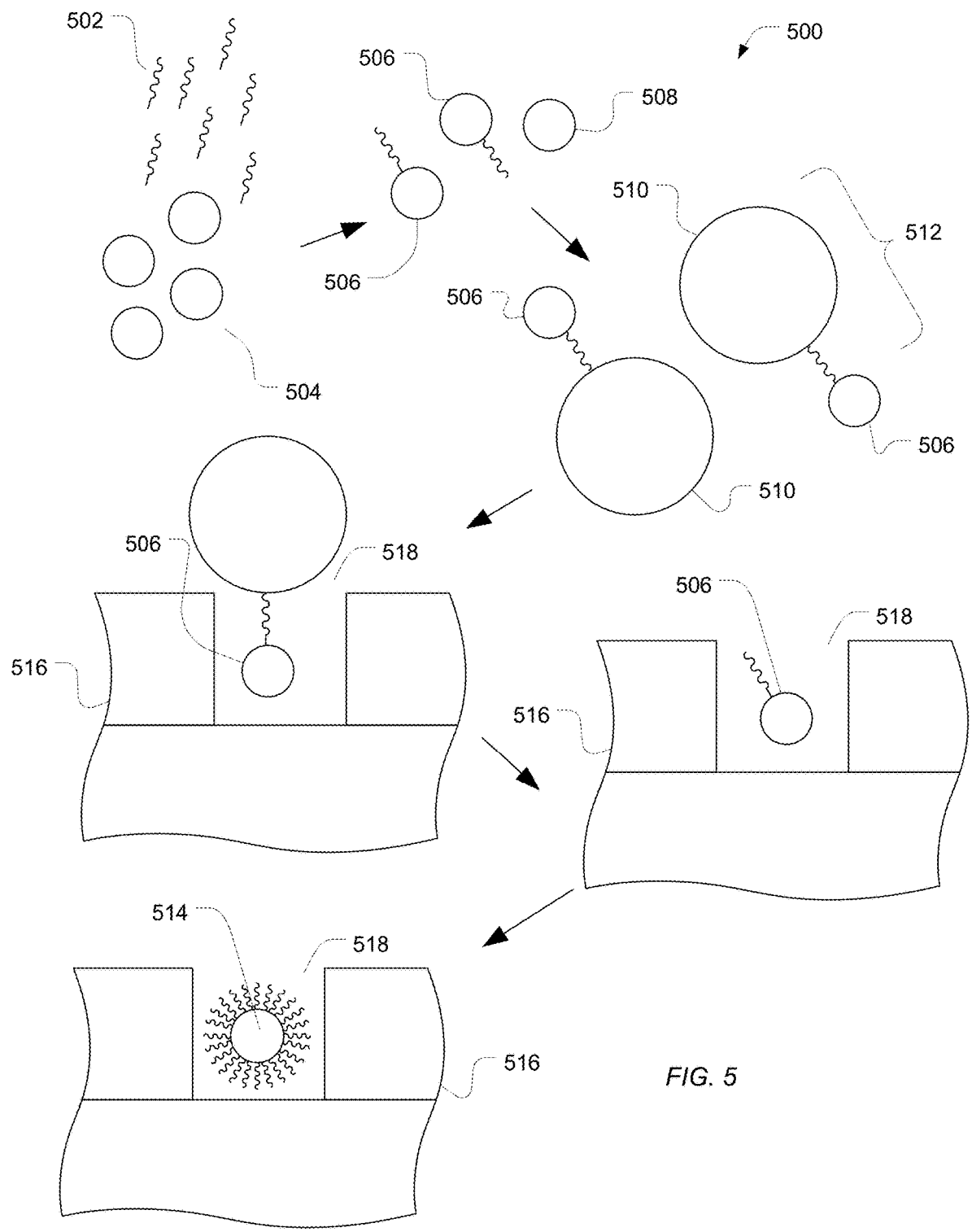

As illustrated in FIG. 5, a plurality of bead supports 504 can be placed in a solution along with a plurality of polynucleotides 502 (target or template poylnucleotides). The plurality of bead supports 504 can be activated or otherwise prepared to bind with the polynucleotides 502. For example, the bead supports 504 can include an oligonucleotide (capture primer) complementary to a portion of a polynucleotide of the plurality of polynucleotides 502. In another example, the bead supports 504 can be modified with target polynucleotides 502 using techniques such as biotin-streptavidin binding.

In a particular embodiment of seeding, the hydrophilic particles and polynucleotides are subjected to polymerase chain reaction (PCR) amplification or recombinase polymerase amplification (RPA). In an example, the particles 504 include a capture primer complementary to a portion of the template polynucleotide 502. The template polynucleotide can hybridize to the capture primer. The capture primer can be extended to form beads 506 that include a target polynucleotide attached thereto. Other beads may remain unattached to a target nucleic acid and other template polynucleotide can be free floating in solution.

In an example, the bead support 506 including a target polynucleotide can be attached to a magnetic bead 510 to form a bead assembly 512. In particular, the magnetic bead 510 is attached to the bead support 506 by a double stranded polynucleotide linkage. In an example, a further probe including a linker moiety can hybridize to a portion of the target polynucleotide on the bead support 506. The linker moiety can attach to a complementary linker moiety on the magnetic bead 510. In another example, the template polynucleotide used to form the target nucleic acid attached to beads 506 can include a linker moiety that attaches to the magnetic bead 510. In another example, the template polynucleotide complementary to target polynucleotide attached to the bead support 506 can be generated from a primer that is modified with a linker that attaches to the magnetic bead 510.

The linker moiety attached to the polynucleotide and the linker moiety attached to the magnetic bead can be complementary to and attach to each other. In an example, the linker moieties have affinity and can include: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement. In a particular example, the linker moiety attached to the polynucleotide includes biotin and the linker moiety attached to the magnetic bead includes streptavidin.

The bead assemblies 512 can be applied over a substrate 516 of a sequencing device that includes wells 518. In an example, a magnetic field can be applied to the substrate 516 to draw the magnetic beads 510 of the bead assembly 512 towards the wells 518. The bead support 506 enters the well 518. For example, a magnet can be moved in parallel to a surface of the substrate 516 resulting in the deposition of the bead support 506 in the wells 518.

The bead assembly 512 can be denatured to remove the magnetic bead 510 leaving the bead support 506 in the well 518. For example, hybridized double-stranded DNA of the bead assembly 512 can be denatured using thermal cycling or ionic solutions to release the magnetic bead 510 and template polynucleotides having a linker moiety attached to the magnetic bead 510.

Optionally, the target polynucleotides 506 can be amplified, referred to herein as templating, while in the well 518, to provide a bead support 514 with multiple copies of the target polynucleotides. In particular, the bead 514 has a monoclonal population of target polynucleotides. Such an amplification reactions can be performed using polymerase chain reaction (PCR) amplification, recombination polymerase amplification (RPA) or a combination thereof.

In a particular embodiment, an enzyme such as a polymerase is present, bound to, or is in close proximity to the particles or beads. In an example, a polymerase is present in solution or in the well to facilitate duplication of the polynucleotide. A variety of nucleic acid polymerase may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

While the polynucleotides of bead support 514 are illustrated as being on a surface, the polynucleotides can extend within the bead support 514. Hydrogel and hydrophilic particles having a low concentration of polymer relative to water can include polynucleotide segments on the interior of and throughout the bead support 514 or polynucleotides can reside in pores and other openings. In particular, the bead support 514 can permit diffusion of enzymes, nucleotides, primers and reaction products used to monitor the reaction. A high number of polynucleotides per particle produces a better signal.

In an exemplary embodiment, the bead support 514 can be utilized in a sequencing device. For example, a sequencing device 516 can include an array of wells 518.

In an example, a sequencing primer can be added to the wells 518 or the bead support 514 can be pre-exposed to the primer prior to placement in the well 518. In particular, the bead support 514 can include bound sequencing primer. The sequencing primer and polynucleotide form a nucleic acid duplex including the polynucleotide (e.g., a template nucleic acid) hybridized to the sequencing primer. The nucleic acid duplex is an at least partially double-stranded polynucleotide. Enzymes and nucleotides can be provided to the well 518 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 516 and can migrate to the well 518. Excitation energy can be also provided to the well 518. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 518 can change. Such a change in pH can be detected by ion sensitive field effect transistors (ISFET). As such, a change in pH can be used to generate a signal indicating the order of nucleotides complementary to the polynucleotide of the particle 510.

In embodiments, the FET may be a FET array. As used herein, an "array" is a planar arrangement of elements such as sensors or wells. The array may be one or two dimensional. A one-dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

One exemplary system involving sequencing via detection of ionic byproducts of nucleotide incorporation is the Ion Torrent PGM™ sequencer, Proton™ sequencer, or S5™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer, Proton™ sequencer, or S5™ sequencer detects the nucleotide incorporations by detecting the hydrogen ion byproducts of the nucleotide incorporations. The Ion Torrent PGM™ sequencer, Proton™ sequencer, or S5™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Figure 6:
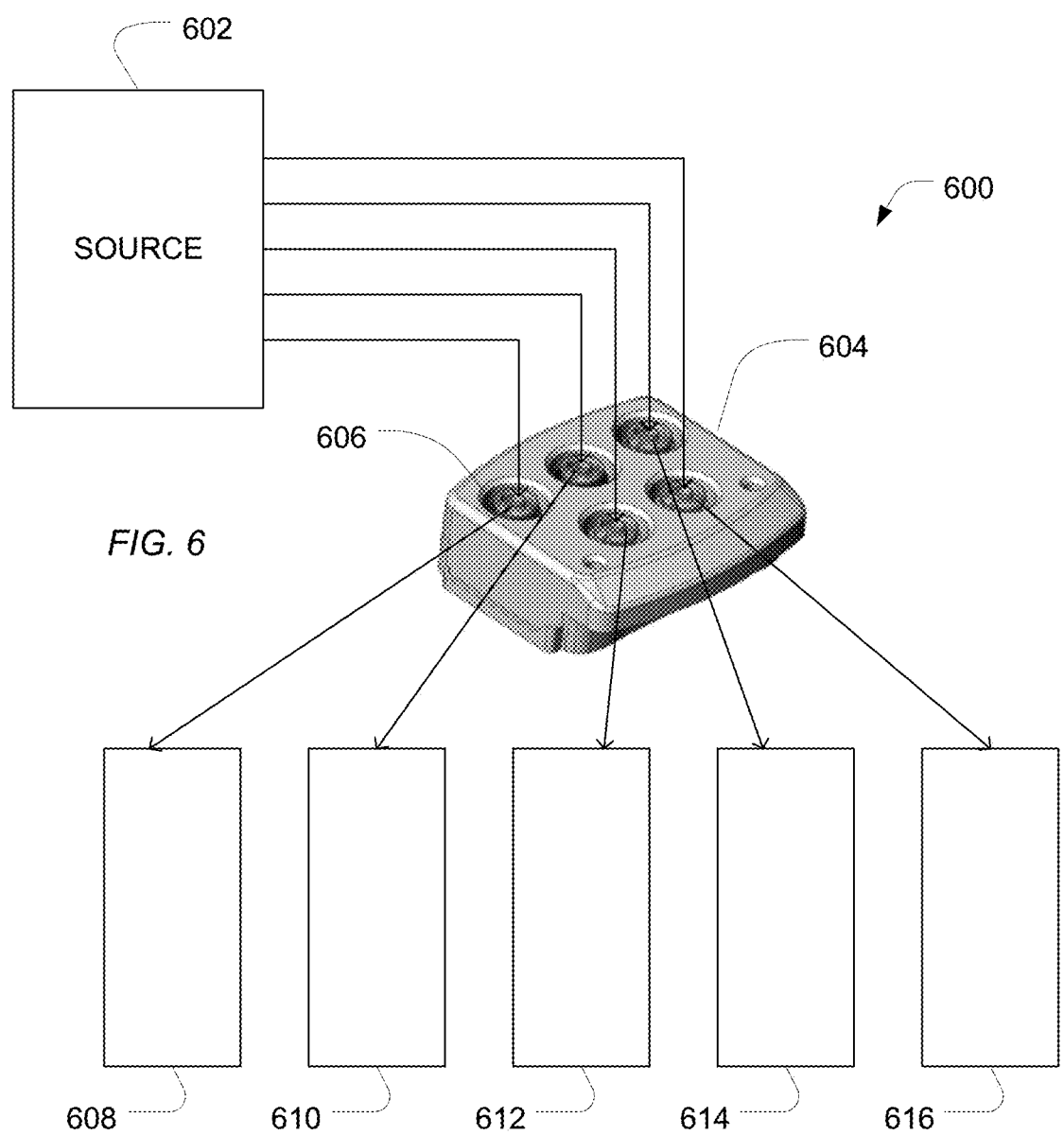
FIG. 6 includes an illustration of an example system for preparing reagents in a sequencing system.

FIG. 6 includes illustration of an exemplary system for preparing reagent solutions in a sequencing device. In an example, a source 602 of an initial solution can be connected to containers within a cartridge 604. The initial solution can include salts, surfactants, and preservatives.

The cartridge 604 can include containers 606 storing a concentrate of reagents to be used in the sequencing reaction. For example, the containers 606 can include a concentrated nucleotide, a concentrated modified nucleotide, or a blend of nucleotides. In another example, the container 606 can include cofactors and enzymes useful in sequencing.

The concentrated nucleotide can be blended with the initial solution, yielding a nucleotide solution to be stored in separate containers, such as containers 608, 610, 612, 614, or 616. In particular, the reagent storage container (606, 610, 612, 614, or 616) can be part of the system illustrated in FIG. 1 having reagent storage containers 104, 106, 108, 110, or 112.

The source 602 can be a pressurized system to instigate flow through the cartridge 604. Alternatively, solutions can be pumped to the cartridge 604 from the source 602. In another example, a vacuum may be drawn in the containers (608, 610, 612, 614, or 616) draw solution through the cartridge and into the containers. In another example, flow can be instigated by both drawing a vacuum and pressurizing or pumping.

Figure 7:
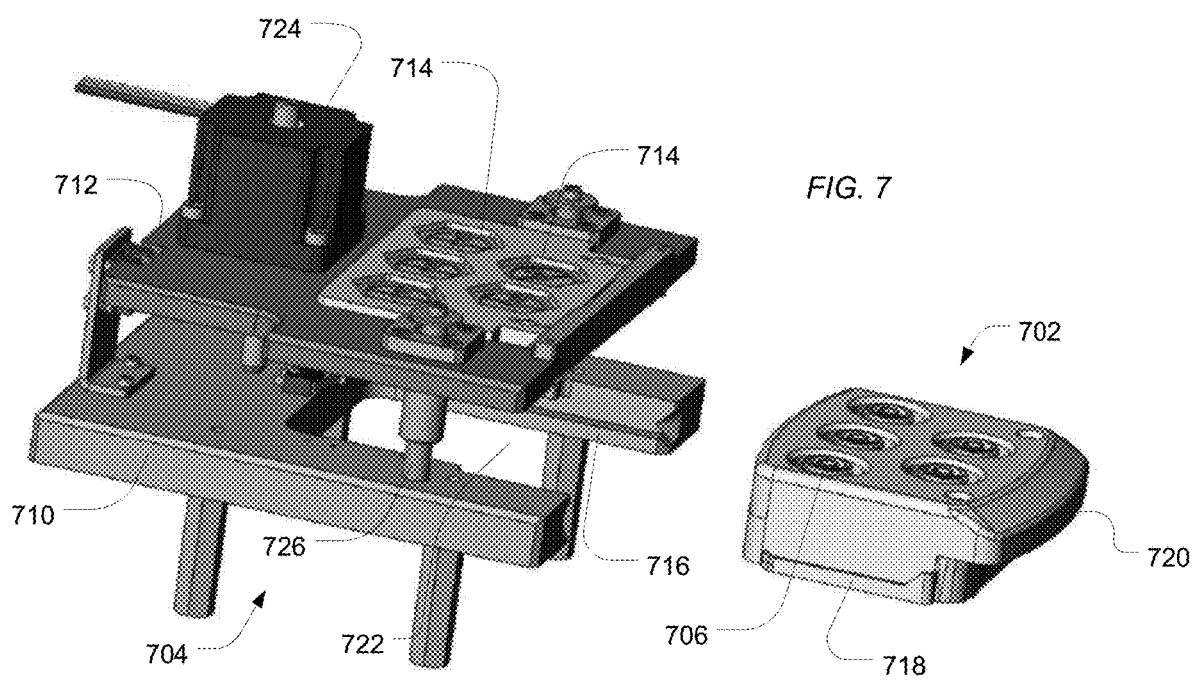
Figure 8:
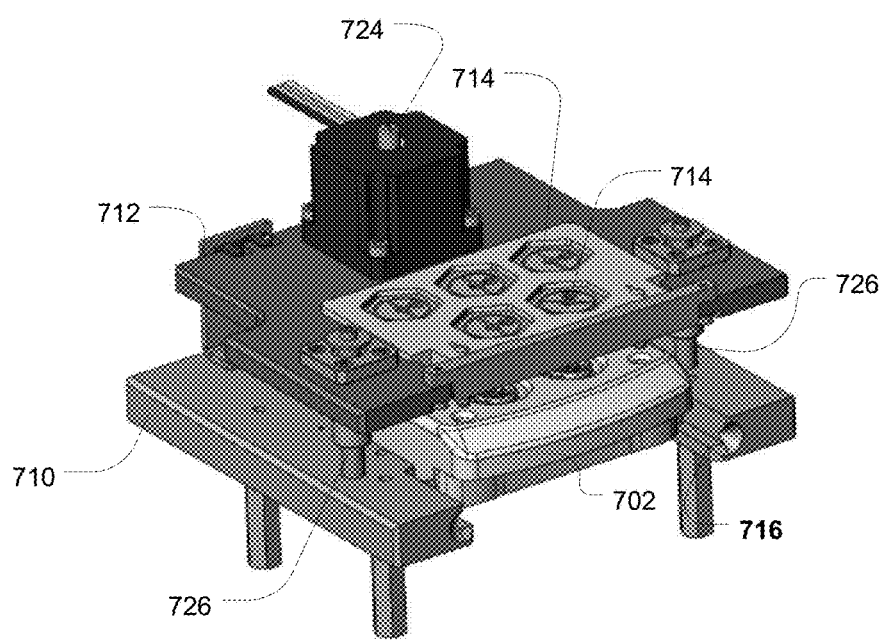

FIG. 7 illustrates an example cartridge system including a cartridge 702 and a docking station 704. The cartridge 702 can fit in a docking area 722 of a primary platform 710 of the docking station 704. In particular, the docking station 704 can include guides, such as rails 716, that cooperate with other guides, such as rails 718 on the cartridge 702, to position the cartridge 702 in the docking station 704, for example as illustrated in FIG. 8. The cartridge 702 can further include a handle 720 to assist with inserting the cartridge 702 and removing the cartridge 702 from the dock 704.

The docking station 704 includes a second platform 712 movable relative to the first platform 710. For example, the platform 712 can be driven relative to the platform 710 by a driver 724, such as a motor or screw mechanism. In particular, the platform 712 can be guided up and down by guides 726.

The platform 712 includes fluid couplers 714 that can be attached to tubing on the top side and interface with the containers 706 of the cartridge 702. As illustrated in FIG. 9, when the cartridge 702 is inserted into the dock 704, and secured by the platform 710, the platform 712 can be driven downward or towards the platform 710 by driver 724 so that the fluidic couplers 714 can engage the containers 706 of the cartridge 702. In particular, guides 726 can ensure positioning of the fluidic couplers 714 relative to the cartridge 702.

Turning to FIG. 10, the cartridge 702 includes a plurality of containers 706. For example, the cartridge can include a number of containers 706 at least equal to the number of nucleotides (i.e., 4). As illustrated, the cartridge 702 has 5 container and may have more or fewer than 5. The cartridge 702 can further include additional reagent concentrate containers, for example including a combination of nucleotides, other ionic compositions, enzymes, or surfactants.

The cartridge 702 also includes a guide 718, illustrated as a rail, to guide the cartridge 702 when engaging the dock 704. The cartridge also can include a handle 720 to assist with insertion and removal of the cartridge from the docking station 704. Further, the cartridge can include positioning features, such as indentations 1030, useful in ensuring that the fluidic couplers 714 are positioned properly to engage the containers 706.

FIG. 11 includes an illustration of an exemplary container 706. The container 706 includes a receiver 1102, a clip 1104, and the seal 1106. The seal 1106 includes a central bore 1110 and at least one peripheral bore 1108 positioned radially outward from the central bore 1110.

As illustrated in FIG. 12, in cross-section, the containers 706 can further include a frit 1212 disposed in a cavity 1216 of the receiver 1102. The frit 1212 can include a central bore 1214 aligned with the central bore 1110 of the seal 1106. The cavity 1216 can also be in fluidic communication with the peripheral openings 1108. Fluid can be applied to the central bore 1110, which flows down through the frit 1212 and into the cavity 1216. The fluid then flows out of the outer holes 1108 and into a channel 1218 of the seal 1106.

Figure 22:
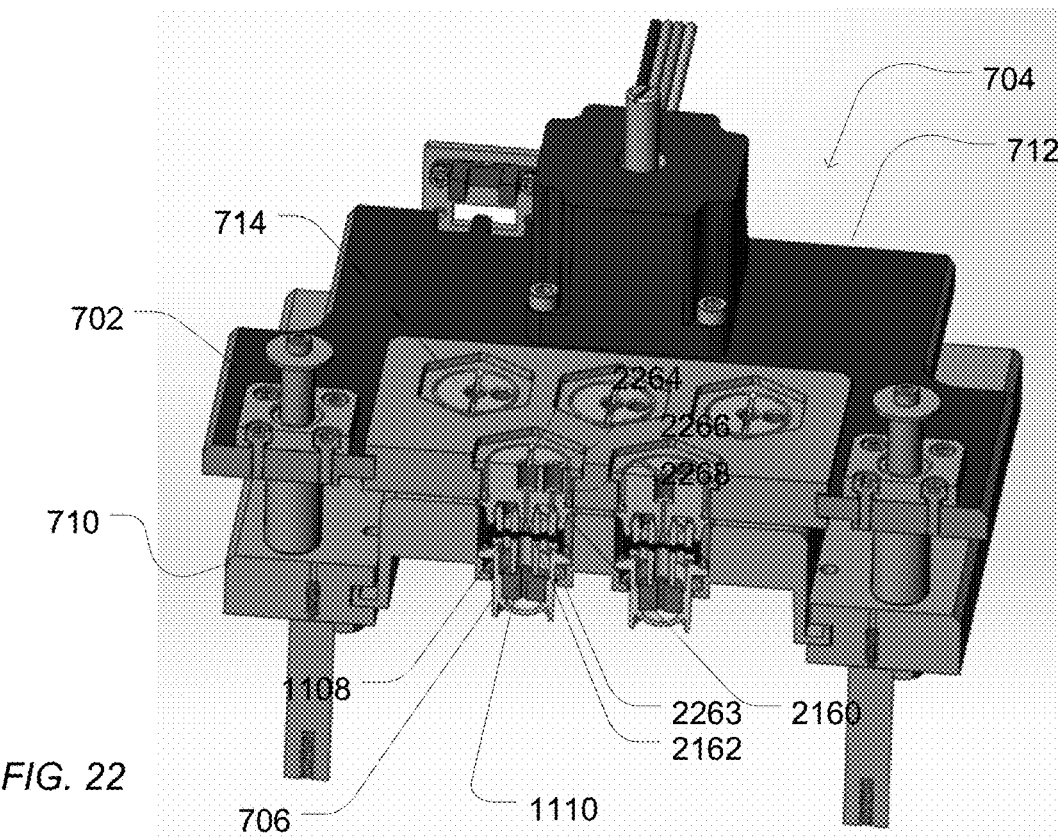

As illustrated in FIG. 13 and FIG. 14, a receiver 1102 can include a ridge 1320 to engage the housing of the cartridge 702, for example, at a lip 2263 (FIG. 22). In addition, the receiver 1102 can include a bar 1322 defining an opening 1324 positioned circumferentially around the upper portion of the receiver 1102. Such a bar 1322 can be used to engage the clip 1104. The receiver 1102 can further include a lip 1325 that engages the seal 1106 when a ridge 1530 (FIG. 15) of the clip 1104 engages the bar 1322.

As illustrated in FIG. 14, the receiver 1102 can define a cavity 1216 between the frit 1212 and the seal 1106. The cavity 1216 can be in fluid communication with the peripheral opening of the seal 1106. The receiver 1102 can further include structures 1426 to engage and position the frit 1212 within the receiver 1102.

Figure 17:
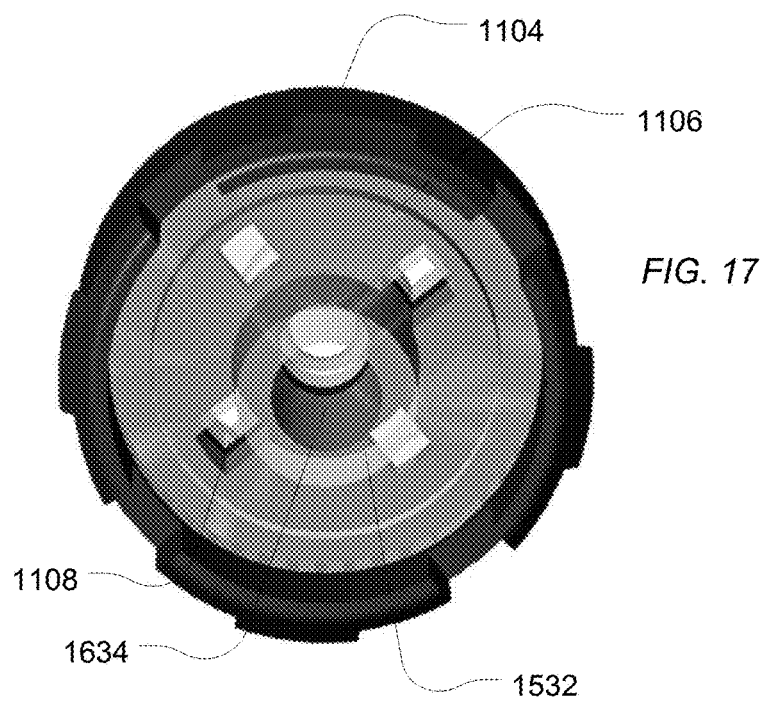

FIG. 15, FIG. 16, and FIG. 17 include illustrations of an exemplary clip 1104 and seal 1106. As illustrated in FIG. 15, the clip 1104 can include a ridge 1530 to engage the bar 1322 of the receiver 1102. The seal 1106 can include a protrusion 1532 defining part of the central bore 1634 that engages the frit 1212.

Figure 18:
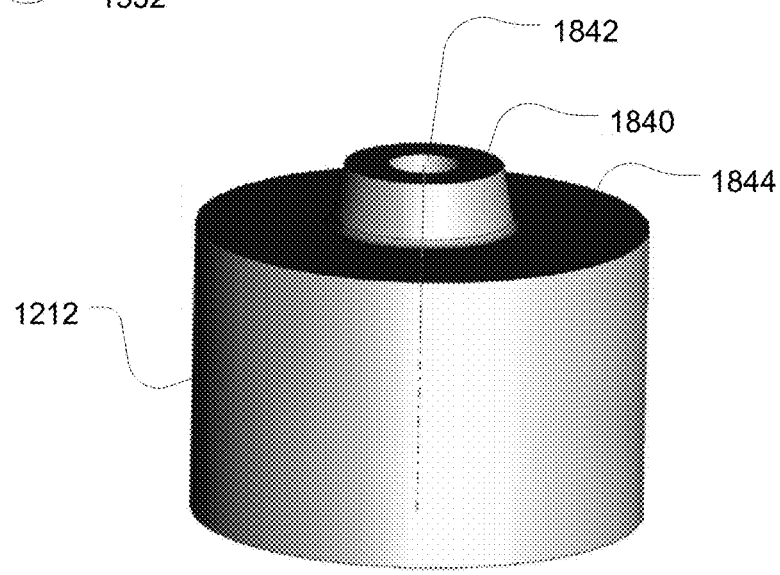

A frit 1212, as illustrated in FIG. 18, can include a protrusion 1840 at a top surface configured to engage the central bore 1634 of the seal 1106. In particular, the protrusion 1840 of the frit can enter a central bore 1634 of the seal 1106 at the protrusion 1532 of the seal 1106. The frit 1212 can be fluid permeable. For example, the frit 1212 can be formed of a porous material, such as a porous ceramic or metallic material. In another example, the frit 1212 can be formed of a porous polymeric material or a water permeable polymer or fibrous material. The frit 1212 can include a central bore 1842 extending at least partially into the frit 1212 or completely through the frit 1212. In addition, the frit 122 includes a larger surface area 1844 at the top through which a solution can flow through the frit to remove concentrated nucleotide solution or reagent solution from the frit and into the cavity 1216 of the receiver 1102.

Figure 19:
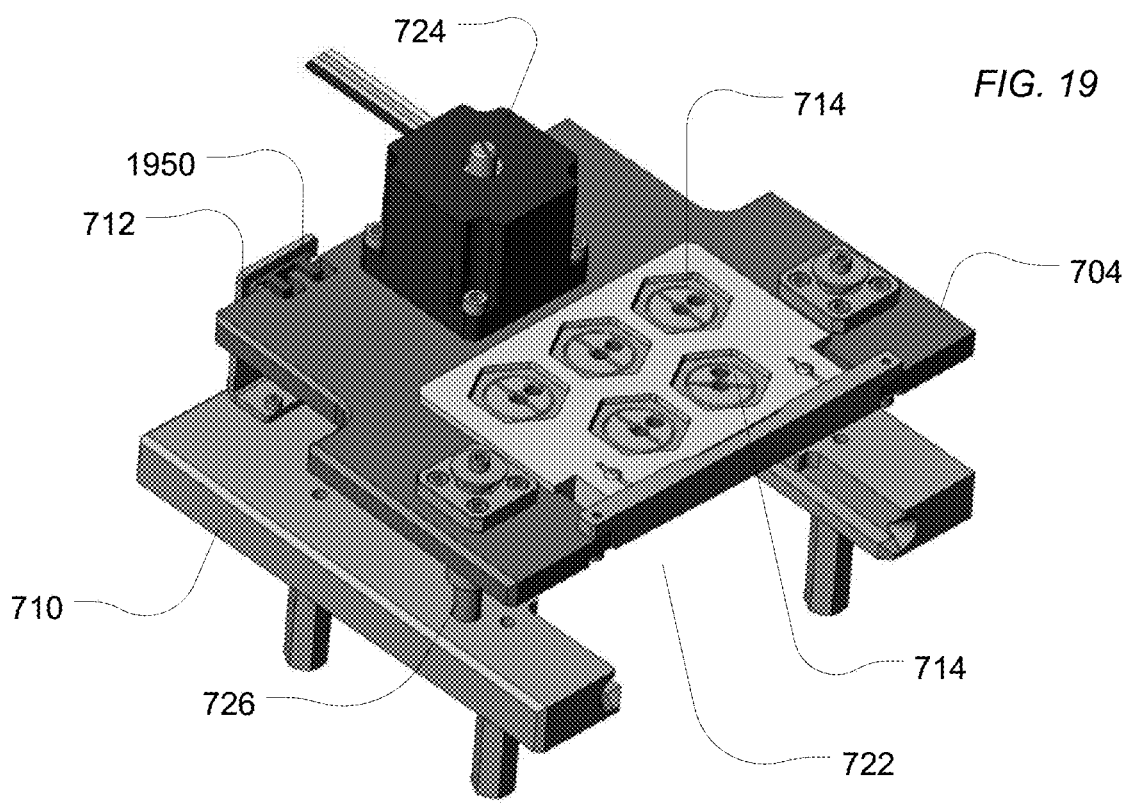
FIG. 19, FIG. 20, FIG. 21 and FIG. 22 include illustrations of an example docking station to receive a cartridge.
Figure 20:
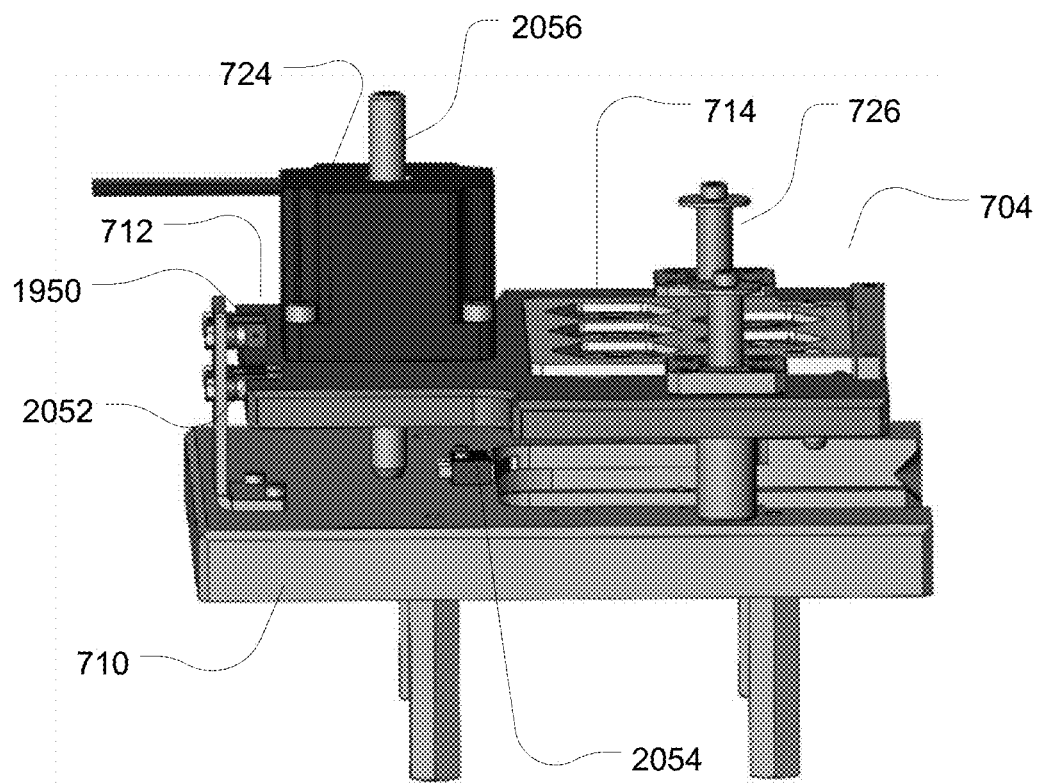

Returning to the docking station, FIG. 19, FIG. 20, FIG. 21, and FIG. 22 include illustrations of the docking station. The docking station can further include sensors, such as sensor 1950, to determine a position of the docking station platforms. For example, as illustrated in FIG. 19, the docking station can be positioned in an upper position in which the platform 712 is further from the platform 710 and is detected by the sensor 1950. When the docking station is lowered or moved in closer proximity from the platform 712 to the platform 710, a second sensor 2052 can detect the presence of the platform 712 in the lower position, as illustrated in FIG. 20. In an example, the sensors 1950 and 2052 are optical sensors which detect the presence of the dock platform 712 at different positions.

A sensor 2054 can also be positioned on the platform 710 to detect the presence of a cartridge. In particular, the sensor 2054 can be a switch sensor activated when the cartridge is in the proper position.

Figure 21:
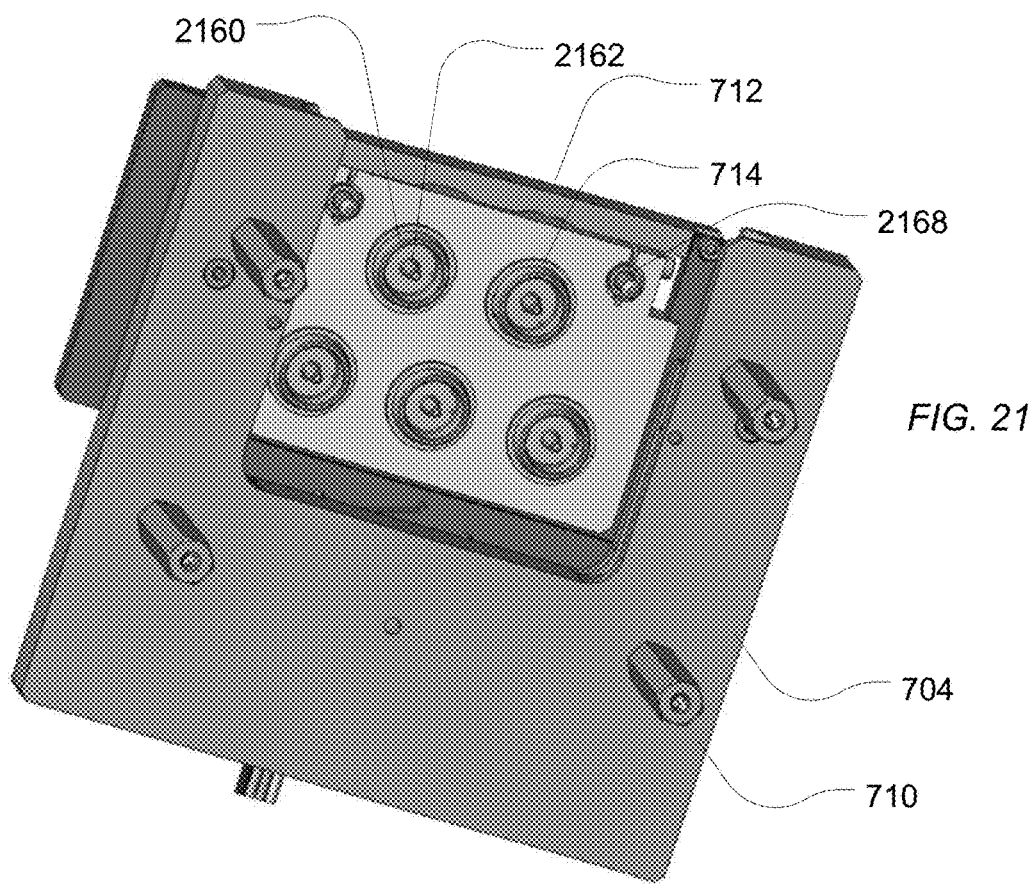

FIG. 21 illustrates a bottom view of the dock 704, which also illustrates the underside of the fluidic couplers 714 attached to the platform 712. In particular, the fluidic couplers 714 can include a tube 2162 disposed on a center axis and a concentric ring 2160 connect to form a seal with the containers 706. The platform 712 can further include guide rods 2168 to engage the indentations 1030 of the cartridge 702.

For example, as illustrated in FIG. 22, when the cartridge 702 is inserted into the dock 704 and the platform 712 is positioned proximity to the platform 710, the fluidic couplers 714 engage the containers and in particular, the seal 1106 of the container 706. A central tube 2162 of the fluidic couplers 714 enters the central bore 1110 of the seal 1106. The outer concentric ring 2160 engages the seal 1106 radially outward of the channel 1218, enclosing the channel 1218. The fluidic couplers 714 further include openings to engage tubes 2264 and 2266. In an example, an opening 2264 is positioned at an axial center of the fluidic couplers 714 and a second opening 2266 is disposed radially outwardly from the central axis of the fluidic couplers 714.

In a particular example, fluid can flow into the opening 2264 and be driven down the tube 2160 into the central bore 1110 of the seal 1106. The fluid flows through the frit 1212 and into the cavity 1216 of the receiver 1102. The fluid can flow through the openings 1108 into the channel 1218 enclosed by the fluidic coupler 714. The fluid can leave the channel 1218 through a hole 2268 connected to the opening 2266. Alternatively, the flow can be reversed.

Figure 23:
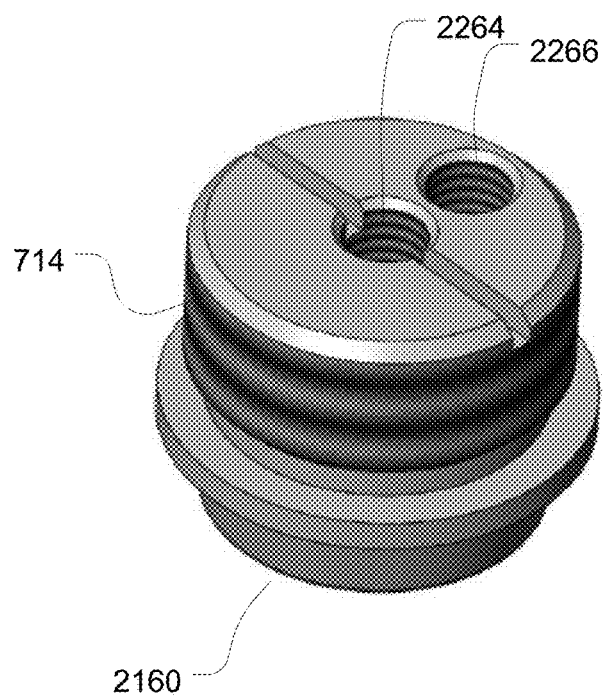
FIG. 23, FIG. 24, and FIG. 25 include illustrations of an example fluidic coupler.
Figure 24:
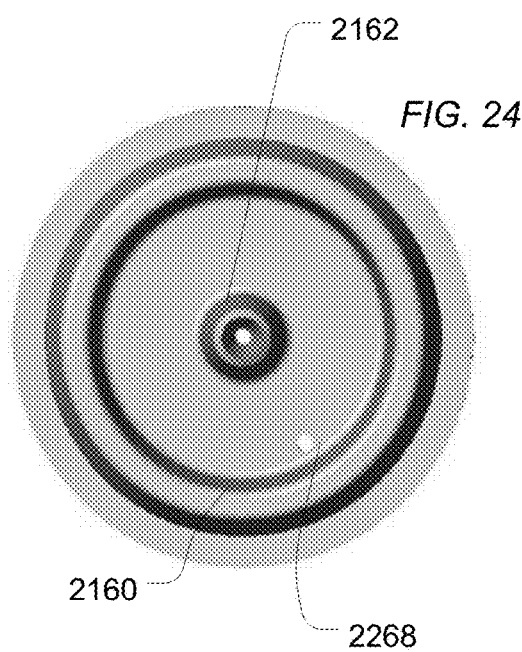
Figure 25:
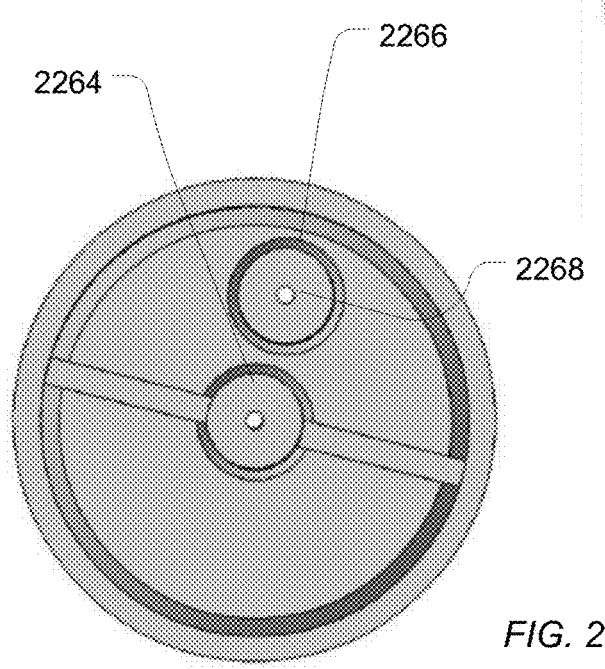

FIG. 23, FIG. 24, and FIG. 25 include illustrations of an exemplary fluidic coupler 714. As above, the fluidic coupler 714 includes the central opening 2264 and a radially outward opening 2266 extending through the fluidic coupler. The central opening 2264 connects with the tube 2162 to provide fluid to the seal or a central bore 1110 of the seal 1106. An outer ring 2160 is disposed radially outward of the central tube 2162 to provide an external seal with or surrounding the seal 1106. An opening 2268 extends to the opening 2266, permitting fluid to leave the channel 1218 in the seal 1106.

In a first embodiment, a method for preparing a nucleotide solution includes, in a system comprising a cartridge connected to a sequencing instruments, the cartridge including a plurality of containers, each container of the plurality of containers having a frit in which a nucleotide concentrate is disposed, flowing a volume of an aqueous solution from an initial solution storage of a sequencing instrument continuously through a container of the plurality of containers fluidically coupled to the sequencing instrument, the aqueous solution flowing through the frit to gather nucleotide from the nucleotide concentrate; and collecting the aqueous solution with nucleotide in a reagent storage container.

In an example of the first embodiment, the nucleotide concentrate is a concentrated solution. For example, the nucleotide concentrate is lyophilized nucleotide.

In another example of the first embodiment and the above examples, the container includes a receptacle, a clip, and a seal, the clip securing the seal to the receptacle, the seal and receptacle enclosing the frit. For example, the seal includes a central bore and a peripheral opening providing fluidic access to the frit. In an example, flowing includes flowing into the container through the central bore of the seal and out of the container through the peripheral opening.

In a further example of the first embodiment and the above examples, the method further includes inserting the cartridge into the sequencing instrument. In an example, the sequencing instrument includes a docking station having a first platform including a second guide mechanism to receive the cartridge and complementary to the guide mechanism of the cartridge and a second platform moveable relative to the first platform and including a fluidic interface having a plurality of fluidic connectors, each fluidic connector including a tube to engage an inlet of a container of the plurality of containers of the cartridge and including an outer ridge to enclose the outlet of the container; wherein inserting the cartridge includes inserting the cartridge into the docking station. For example, each fluidic connector includes a first port in fluid communication with the tube of the fluidic connector and the inlet of the container and including a second port in fluid communication with the outlet of the container. In another example, the sequencing instrument comprises a plurality of reagent storage containers, each of the fluidic connectors uniquely in fluid communication with a reagent storage container of the plurality of reagent storage containers. In a further example, the docking station further includes a drive mechanism to move the second platform relative to the first platform, and wherein inserting the cartridge into the sequencing instrument includes moving the second platform closer to the first platform. For example, the docking station includes a position sensor to determine a position of the second platform relative to the first platform, wherein moving the second platform closer to the first platform includes detecting a position of the second platform relative to the first platform. In another example, the docking station includes a cartridge sensor to detect the presence of the cartridge, wherein moving the second platform closer to the first platform is responsive to detecting the presence of the cartridge.

In a second embodiment, a system for preparing a nucleotide solution includes a cartridge having a housing having first and second major surfaces and defining a guide mechanism; a plurality of containers disposed in the housing, each container of the plurality of containers having a receptacle and a lid, the lid formed of a clip and a seal, a frit disposed in the receptacle in an enclosed space defined by the receptacle and the seal, the seal having an inlet and an outlet in fluid communication with an enclosed space, the frit including a nucleotide concentrate. The system further includes a docking station having a first platform including a second guide mechanism to receive the cartridge and complementary to the guide mechanism of the cartridge; and a second platform moveable relative to the first platform and including a fluidic interface having a plurality of fluidic connectors, each connector including a tube to engage an inlet of a container of the plurality of containers of the cartridge and including an outer ridge to enclose the outlet of the container.

In an example of the second embodiment, each connector includes a first port in fluid communication with the tube of the connector and the inlet of the container and including a second port in fluid communication with the outlet of the container.

In another example of the second embodiment and the above examples, the system further includes an initial solution storage container in fluid communication with the fluidic interface.

In a further example of the second embodiment and the above examples, the system further includes a plurality of reagent storage containers, each of the fluidic connectors uniquely in fluid communication with a reagent storage container.

In an additional example of the second embodiment and the above examples, a drive mechanism to move the second platform relative to the first platform.

In another example of the second embodiment and the above examples, the system further includes a position sensor to determine a position of the second platform relative to the first platform.

In a further example of the second embodiment and the above examples, the system further includes a cartridge sensor to detect the presence of the cartridge.

In an additional example of the second embodiment and the above examples, the system further includes rods disposed under the second platform to engage indentations in the cartridge to ensure alignment of the plurality of containers with the fluid connectors of the fluid interface.

In another example of the second embodiment and the above examples, the frit is fluid permeable.

In a further example of the second embodiment and the above examples, the seal includes a central bore and a peripheral opening providing fluidic access to the frit.

In an additional example of the second embodiment and the above examples, the seal includes a protrusion to engage a protrusion of the frit. For example, the protrusion of the frit fits in the central bore of the seal. In an example, the frit includes a central bore in fluid communication with the central bore the of the seal. In another example, a cavity is defined between the frit and the seal, the cavity in fluid communication with the peripheral opening of the seal.

In another example of the second embodiment and the above examples, the clip includes a ridge to engage a bar of the receiver. For example, the seal engages a lip of the receiver when the ridge of the clip engages the bar of the receiver.

In a further example of the second embodiment and the above examples, the receiver can include a ridge to engage a lip of the housing.

In a third embodiment, a cartridge includes a housing having first and second major surfaces and defining a guide mechanism; and a plurality of containers disposed in the housing, each container of the plurality of containers having a receptacle and a lid, the lid formed of a clip and a seal, the clip to secure the seal to the receptacle, a frit disposed in the receptacle in an enclosed space defined by the receptacle and the seal, the seal having an inlet and an outlet in fluid communication with an enclosed space, the frit including a nucleotide concentrate.

In an example of the third embodiment, the nucleotide concentrate is a concentrated solution.

In another example of the third embodiment and the above examples, the nucleotide concentrate is lyophilized nucleotide.

In a further example of the third embodiment and the above examples, the frit is fluid permeable.

In an additional example of the third embodiment and the above examples, the seal includes a central bore and a peripheral opening providing fluidic access to the frit. For example, the seal includes a protrusion to engage a protrusion of the frit. In an example, the protrusion of the frit fits in the central bore of the seal. In another example, the frit includes a central bore in fluid communication with the central bore the of the seal. In a further example, a cavity is defined between the frit and the seal, the cavity in fluid communication with the peripheral opening of the seal.

In another example of the third embodiment and the above examples, the clip includes a ridge to engage a bar of the receiver. For example, the seal engages a lip of the receiver when the ridge of the clip engages the bar of the receiver.

In a further example of the third embodiment and the above examples, the receiver can include a ridge to engage a lip of the housing.

In a fourth embodiment, a system for preparing a nucleotide solution includes a cartridge having a housing having first and second major surfaces and defining a guide mechanism; a plurality of containers disposed in the housing, each container of the plurality of containers having a receptacle and a lid, the lid formed of a clip and a seal, a frit disposed in the receptacle in an enclosed space defined by the receptacle and the seal, the seal having an inlet and an outlet in fluid communication with an enclosed space. The system further includes a docking station having a first platform including a second guide mechanism to receive the cartridge and complementary to the guide mechanism of the cartridge; and a second platform moveable relative to the first platform and including a fluidic interface having a plurality of fluidic connectors, each connector including a tube to engage an inlet of a container of the plurality of containers of the cartridge and including an outer ridge to enclose the outlet of the container.

In an example of the fourth embodiment, each connector includes a first port in fluid communication with the tube of the connector and the inlet of the container and including a second port in fluid communication with the outlet of the container.

In another example of the fourth embodiment and the above examples, the system further includes an initial solution storage container in fluid communication with the fluidic interface.

In a further example of the fourth embodiment and the above examples, the system further includes a plurality of reagent storage containers, each of the fluidic connectors uniquely in fluid communication with a reagent storage container.

In an additional example of the fourth embodiment and the above examples, a drive mechanism to move the second platform relative to the first platform.

In another example of the fourth embodiment and the above examples, the system further includes a position sensor to determine a position of the second platform relative to the first platform.

In a further example of the fourth embodiment and the above examples, the system further includes a cartridge sensor to detect the presence of the cartridge.

In an additional example of the fourth embodiment and the above examples, the system further includes rods disposed under the second platform to engage indentations in the cartridge to ensure alignment of the plurality of containers with the fluid connectors of the fluid interface.

In another example of the fourth embodiment and the above examples, the frit is fluid permeable.

In a further example of the fourth embodiment and the above examples, the seal includes a central bore and a peripheral opening providing fluidic access to the frit.

In an additional example of the fourth embodiment and the above examples, the seal includes a protrusion to engage a protrusion of the frit. For example, the protrusion of the frit fits in the central bore of the seal. In an example, the frit includes a central bore in fluid communication with the central bore the of the seal. In another example, a cavity is defined between the frit and the seal, the cavity in fluid communication with the peripheral opening of the seal.

In another example of the fourth embodiment and the above examples, the clip includes a ridge to engage a bar of the receiver. For example, the seal engages a lip of the receiver when the ridge of the clip engages the bar of the receiver.

In a further example of the fourth embodiment and the above examples, the receiver can include a ridge to engage a lip of the housing.

In a fifth embodiment, a cartridge includes a housing having first and second major surfaces and defining a guide mechanism; and a plurality of containers disposed in the housing, each container of the plurality of containers having a receptacle and a lid, the lid formed of a clip and a seal, the clip to secure the seal to the receptacle, a frit disposed in the receptacle in an enclosed space defined by the receptacle and the seal, the seal having an inlet and an outlet in fluid communication with an enclosed space.

In an example of the fifth embodiment, the nucleotide concentrate is a concentrated solution.

In another example of the fifth embodiment and the above examples, the nucleotide concentrate is lyophilized nucleotide.

In a further example of the fifth embodiment and the above examples, the frit is fluid permeable.

In an additional example of the fifth embodiment and the above examples, the seal includes a central bore and a peripheral opening providing fluidic access to the frit. For example, the seal includes a protrusion to engage a protrusion of the frit. In an example, the protrusion of the frit fits in the central bore of the seal. In another example, the frit includes a central bore in fluid communication with the central bore the of the seal. In a further example, a cavity is defined between the frit and the seal, the cavity in fluid communication with the peripheral opening of the seal.

In another example of the fifth embodiment and the above examples, the clip includes a ridge to engage a bar of the receiver. For example, the seal engages a lip of the receiver when the ridge of the clip engages the bar of the receiver.

In a further example of the fifth embodiment and the above examples, the receiver can include a ridge to engage a lip of the housing.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for preparing a nucleotide solution, the method comprising:
   in a system comprising a cartridge connected to a sequencing instrument, the cartridge including a plurality of containers, each container of the plurality of containers having a frit in which a nucleotide concentrate is disposed, the each container including a receptacle, a clip, and a seal, the clip securing the seal to the receptacle, the seal and receptacle enclosing the frit, the seal including a central bore and a peripheral opening providing fluidic access to the frit;
   flowing a volume of an aqueous solution from an initial solution storage of the sequencing instrument continuously through a container of the plurality of containers fluidically coupled to the sequencing instrument, the aqueous solution flowing through the fit to gather nucleotide from the nucleotide concentrate, wherein flowing includes flowing into the container through the central bore of the seal and out of the container through the peripheral opening; and
   collecting the aqueous solution with the nucleotide in a reagent storage container.

2. The method of claim 1, wherein the nucleotide concentrate is a concentrated solution.

3. The method of claim 1, wherein the nucleotide concentrate is lyophilized nucleotide.

4. The method of claim 1, further comprising inserting the cartridge into the sequencing instrument.

5. The method of claim 4, wherein the sequencing instrument comprises:
   a docking station having:
   a first platform including a second guide mechanism to receive the cartridge and complementary to a guide mechanism of the cartridge; and
   a second platform moveable relative to the first platform and including a fluidic interface having a plurality of fluidic connectors, each fluidic connector including a tube to engage an inlet of a container of the plurality of containers of the cartridge and including an outer ridge to enclose an outlet of the container; and wherein inserting the cartridge includes inserting the cartridge into the docking station.

6. The method of claim 5, wherein each fluidic connector includes a first port in fluid communication with the tube of the fluidic connector and the inlet of the container and including a second port in fluid communication with the outlet of the container.

7. The method of claim 5, wherein the sequencing instrument comprises a plurality of reagent storage containers, each of the fluidic connectors uniquely in fluid communication with a reagent storage container of the plurality of reagent storage containers.

8. The method of claim 5, wherein the docking station further includes a drive mechanism to move the second platform relative to the first platform, and wherein inserting the cartridge into the sequencing instrument includes moving the second platform closer to the first platform.

9. The method of claim 8, wherein the docking station includes a position sensor to determine a position of the second platform relative to the first platform, wherein moving the second platform closer to the first platform includes detecting a position of the second platform relative to the first platform.

10. The system of claim 8, wherein the docking station includes a cartridge sensor to detect the presence of the cartridge, wherein moving the second platform closer to the first platform is responsive to detecting the presence of the cartridge.

\* \* \* \* \*

UNITED STATES PATENT AND TRADEMARK OFFICE
CERTIFICATE OF CORRECTION

PATENT NO. : 11,117,129 B2  
APPLICATION NO. : 16/543421  
DATED : September 14, 2021  
INVENTOR(S) : Mark Reed et al.

Page 1 of 1

It is certified that error appears in the above-identified patent and that said Letters Patent is hereby corrected as shown below:

In the Claims

In Column 16, Claim 1, Line 43, delete "through the fit to" and insert -- through the frit to --, therefor.

In Column 17, Claim 10, Line 24, delete "system of" and insert -- method of --, therefor.

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*